United States Patent [19]

Chipens et al.

[11] 4,353,823
[45] Oct. 12, 1982

[54] SYNTHETIC ANALOG OF TUFTISIN

[76] Inventors: Gunar I. Chipens, ulitsa Apes, 12, kv. 81; Nadezhda I. Veretennikova, ulitsa Veyavas, 10/1, kv. 11; Zeltite A. Atare, ulitsa Volguntes, 82, kv. 1, all of Riga, U.S.S.R.

[21] Appl. No.: 298,396
[22] Filed: Sep. 1, 1981
[51] Int. Cl.³ .......................................... C07C 103/52
[52] U.S. Cl. ............................................. 260/112.5 R
[58] Field of Search .................. 260/112.5 R; 424/177

[56] References Cited
FOREIGN PATENT DOCUMENTS
784218  9/1981  U.S.S.R.

Primary Examiner—John F. Terapane
Assistant Examiner—F. T. Moezie
Attorney, Agent, or Firm—Ladas & Parry

[57] ABSTRACT

A synthetic analog of tuftisin, namely: glycyl-lysyl-prolyl-arginine of the formula:

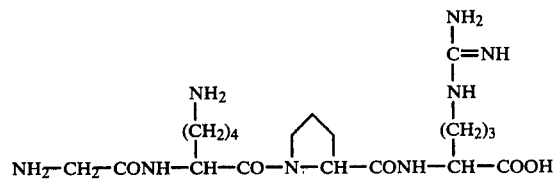

The synthetic analog of tuftisin according to the present invention has a high phagocytosis-stimulating activity when used in small doses.

1 Claim, No Drawings

SYNTHETIC ANALOG OF TUFTISIN

The present invention relates to the art of synthetic peptides and, more specifically, to a novel active analog of naturally-occurring peptide tuftisin possessing, as compared to tuftisin, a higher phagocytosis-stimulant activity.

FIELD OF THE INVENTION

The above-mentioned analog of tuftisin can be useful in medicine as an immunostimulant possessing a wide-range effect.

BACKGROUND OF THE INVENTION

The naturally-occurring phagocytosis-stimulant peptide-tuftisin comprises a fragment of a heavy chain of human immunoglobulins of the class IgG (Thr-Lys-Pro-Arg). This tetrapeptide reveals a stimulant effect relative to numerous immunological reactions both in vivo and in vitro; thus it substantially stimulates the phagocytic activity of leukocytes and macrophages (cf. Cytobios, vol. 6, No. 21–22, 1972; A. Constantopoulos, V. A. Najjar "Tuftisin, a natural and general phagocytosis stimulating peptide affecting macrophages and polymorphonuclear granulocytes", p. 97–100).

It is known from the literature that tuftisin can be useful as a medicated compound for substitution of γ-globulin in the treatment of diseases associated with decreased activity of leukocytes, as well as in spleenectomy and certain disturbances of spleen which are accompanied by considerable reduction of the organism resistance to infectional diseases. (Cf. J. Pediat., vol. 80, No. 4, 1972; A. Constantopoulos, V. A. Najjar, J. W. Smith "Tuftisin deficiency: a new syndrome with defective phagocytosis", pp. 564–567).

Known in the art are numerous synthetic analogs of tuftisin formed by modification of one or two aminoacid moieties of the molecule (Int. J. Peptide Protein Res. Vol. 9, N 1, 1977; D. Konopinska, E. Nawrocka, I. I. Siemion, S. Slopek, St. Szymaniec, E. Klonowska "Partial sequences of histones with tuftisin activity", 71–77, Biochim. Biophys. Acta, Vol. 496, N 1, 1977; M. Fridkin, Y. Stabinsky, V. Zakuth, Z. Spirer "Tuftisin and some analogs. Synthesis and interaction with human polymorphonuclear leykocytes", 203–211).

However, these modified analogs of tuftisin possess but an insufficient phagocytosis-stimulating activity as compared to natural tuftisin.

BRIEF SUMMARY OF THE INVENTION

It is an object of the present invention to provide such a synthetic analog of tuftisin which would possess an increased phagocytosis-stimulating activity and be economically efficient.

This object is accomplished by a synthetic analog of tuftisin, namely: glycyl-lysyl-prolyl-arginine of the formula:

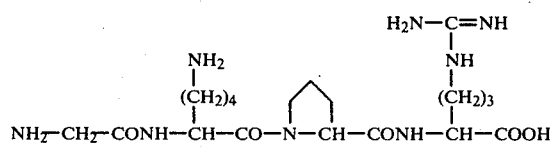

The novel synthetic analog of tuftisin-glycyl-lysyl-prolyl-arginine (Gly-Lys-Pro-Arg) comprises a white amorphous lyophilizate decomposing at a temperature above 110° C. and having a specific rotation $[\alpha]_D^{20} - 62.3°$ (c 0.48; 5% CH$_3$COOH).

The data of aminoacid analysis: Gly—1.1; Lys—0.9; Pro—1.0; Arg—1.0.

The data of electrophoretic analysis: the electrophoretic mobility is determined relative to histidine in 1 N acetic acid using paper FN-16 (GDR) at the voltage of 900 V. For the novel compound according to the present invention $E_{his}$ is 1.10 (pH=2.4).

The data of chromatographic analysis: chromatographic mobility $R_f$=0.16 (n-butanol-pyridine-water-acetic acid in the ratio of 30:2:6:24), using "Merck" plates.

The biological activity of glycyl-lysyl-prolyl-argynine is tested in experiments in vitro. To this end, the effect of the compound is studied on phagocytic activity of segmented neutrophils of rat's blood in comparison with the effect of a known stimulant of phagocytosis-tuftisin (Thr-Lys-Pro-Arg).2CH$_3$COOH.3H$_2$O) prepared at the Institute of Organic Synthesis of Latvian Academy of Sciences. The phagocytic capacity of segmented neutrophils is determined following the procedure by R. S. Gostev (Proceedings of AMN SSSR, Voprosy Pitanija "Role of Protein in Nutrition", vol. 13, iss. 2, 1950, Moscow: V. S. Gostev, M. N. Petryashina, S. A. Popovkina, A. K. Saakov "Phagocytosis, Complement and Blood Coagulation at Protein Deficiency in Food", pp. 110–116).

According to this procedure, for the experiments rat's blood diluted with 2% sodium citrate in the ratio of 1:1 is mixed with the physiological solution of the synthetic analog of tuftisin according to the present invention. Then a day's age culture of a coagulopositive strain Staphylococcusaureus is added in the concentration of 1 bln in 1 ml. The mixture is incubated in a thermostat at the temperature of 37° C. for 30 minutes. Then smears are prepared, fixed wth methanol and coloured according to Romanovsky-Gymza. 100 segmented neutrophils are counted, the number of bacteria-consuming ones is determined (percentage of active phagocytes) and an average number of bacteria in one segmented neutrophil (phagocytic number). The phagocytic characteristics are shown in the Table hereinbelow.

As it is seen from the Table, glycyl-lysyl-prolyl-arginine activates phagocytosis to the same extent as tuftisin per se, but in smaller concentrations.

DETAILED DESCRIPTION OF THE INVENTION

Preparation of glycyl-lysyl-prolyl-arginine is effected in the following manner.

p-Nitrophenyl ester of benzyloxycarbonyl-proline is reacted with arginine to give a dipeptide-benzyloxycarbonylprolyl-arginine.

Then the resulting compound is dissolved in glacial acetic acid, treated with a solution of hydrogen bromide in glacial acetic acid to give prolyl-arginine.

Thereafter, previously prepared prolyl-arginine is reacted with pentafluorophenyl ester of tert.butyloxycarbonyl-N$^\epsilon$-benzyloxycarbonyl-lysine with the formation of a tripeptide-tert.butyloxycarbonyl-N$^\epsilon$-benzyloxycarbonyl-lysyl-prolyl-arginine which is treated with a 70% aqueous solution of trifluoroacetic acid to give N$^\epsilon$-benzyloxycarbonyl-lysyl-prolyl-arginine.

Then the reaction is carried out between pentafluorophenyl ester of benzyloxycarbonyl-glycine and the tripeptide-N$^\epsilon$-benzyloxycarbonyl-lysyl-prolyl-arginine to give benzyloxycarbonyl-glycyl-N⁶-benzyloxycarbonyl-lysyl-prolyl-arginine.

The resulting protected tetrapeptide is deblocked by hydrogenation with the formation of glycyl-lysyl-prolyl-arginine.

TABLE

| Phagocytic indexes Concentration | Phagocytosis-stimulating activity of glycyl—lysyl—prolyl—arginine to rat's blood leukocytes (in comparison with the prototype-tuftisin) | | | | | | | |
|---|---|---|---|---|---|---|---|---|
| | Glycyl—lysyl—prolyl—arginine | | | | Tuftisin | | | |
| | $3 \cdot 10^{-6}$M | $3 \cdot 10^{-7}$M | $3 \cdot 10^{-8}$M | $3 \cdot 10^{-9}$M | $3 \cdot 10^{-6}$M | $3 \cdot 10^{-7}$M | $3 \cdot 10^{-8}$M | $3 \cdot 10^{-9}$M |
| Index of phagocytosis $A/A_k$ | 1.11 | 1.25 | 1.62 | 1.26 | 1.67 | 1.71 | 1.45 | 0.98 |
| Phagocytic stimulation $\frac{P - P_k}{P_k} \cdot 100\%$ | 22 | 23 | 101 | 72 | 125 | 144 | 68 | 4 |

A—number of active leukocytes in the presence of the compound;
$A_k$—number of active leukocytes in the control;
P—number of bacteria consumed by one leukocyte in the presence of the compound;
$P_k$—number of bacteria consumed by one leukocyte in the control.

The general scheme of the synthesis is schematically represented in the following figure.

The novel synthetic analog of tuftisin-glycyl-lysyl-prolyl-arginine possesses a high phagocytosis-stimulating activity in smaller doses as compared to tuftisin.

Furthermore, in the synthesis of tuftisin use is made of rather expensive threonine, wherefore the use of glycine in the synthesis of the analog of tuftisin according to the present invention makes it possible to substantially lower the self cost of the product manufacture.

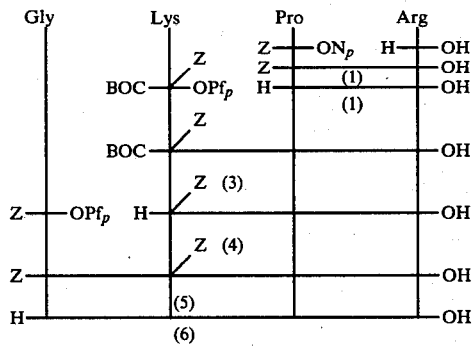

Figure: Scheme of synthesis of glycyl—lysyl—prolyl—arginine.

For a better understanding of the present invention the following specific example is given hereinbelow by way of illustration.

In the synthesis use is made of aminoacids and derivatives thereof available from the "Reanal" Co., Hungary. All the aminoacids, except glycine have the L-configuration. The melting point values determined in open capillaries are given without corrections. The specific rotation is measured on a digital polarimeter Perkin Elmer 141. Electrophoresis of peptides is carried out using the paper FN-16 (GDR) in 1 N (pH=2.4) and 5 N (pH=1.4) acetic acid. Electroforetic mobility values are given relative to histidine ($E_{His}$), as well as chromatographic mobility values on plates "Silufol", "Eastman" and "Merck" in systems: n-butanol-ethanol-acetic acid-water, 80:10:5:30 (A); n-butanol-pyridine-acetic acid-water, 30:20:6:24 (B). The ion-exchange chromatography is carried out using CM-cellulose "Whatman" CM-32; for the provision of the linear gradient of ammonium acetate use is made of the mixer "Ultrograd" (KB, Sweden). Evaporation is carried out in a vacuum rotary evaporator under the residual pressure of from 1 to 10 mm Hg and at the temperature of 30° C.

Benzyloxycarbonyl-prolyl-arginine (I)

To a solution of 37 g (0.1 mol) of p-nitrophenyl ester of benzyloxycarbonylproline in 360 ml of dioxane there is added a solution of 16 g (0.09 mol) of arginine in 160 ml of water under vigorous stirring. Two hours thereafter the solvent is evaporated and the precipitate is dissolved in 100 ml of dimethylformamide. The solution is stirred at room temperature for 72 hours and poured into 1 liter of ethylacetate. The resulting residue is filtered-off, washed on the filter with ethylacetate and reprecipitated from a mixture ethanol-ethylacetate. The yield of product (I) is 35 g (96%); the product has the following properties: M.p. 190° C., $[\alpha]_D^{20} -46.6°$; (c 1.0; H₂O); $R_f = 0.53$ (A, "Silufol") 0.66 (B, "Eastman"); $E_{His} = 0.56$ (pH=2.4).

Tert.butyloxycarbonyl-N⁶-benzyloxycarbonyl-lysyl-prolyl-arginine (3)

(a) 35 g (0.086 mol) of benzyloxycarbonyl-prolyl-arginine (I) are treated with 250 ml of 2 N HBr/CH₃COOH for one hour. The resulting mixture is evaporated to dryness and the residue is rubbed with dry diethyl ether.

The resulting residue is filtered-off, dried in vacuum and dissolved in 500 ml of water. The solution is treated with an anionite to the negative reaction on bromine ions and evaporated to dryness. The yield of prolyl-arginine (2) is quantitative (23 g). The product has the following properties: $R_f = 0.00$ (A, "Silufol"); $E_{His} = 0.95$ (pH=1.4).

(b) 23 g (0.086 mol) of prolyl-arginine (2) are dissolved in 100 ml of water and to this solution under stirring there is added a solution of 53 g (0.1 mol) of pentafluorophenyl ester of tert.butyloxycarbonyl-N⁶-benzyloxycarbonyl-lysine in 300 ml of dioxane. 2 hours thereafter the solvent is evaporated and the residue is dissolved in 150 ml of dimethylformamide and stirred at room temperature (20° C.) for 48 hours. Then dimethylformamide is evaporated to ⅓ of its volume and the solution is poured into one liter of ether. After 2 hours the resulting residue is filtered-off, washed on the filter with ether and dried in vacuum. After reprecipitation from a mixture ethylacetate-ethanol-ether (3:1:30) there are obtained 47 g (74%) of the product (3) having the following properties: M.p. 90° C., $[\alpha]_D^{20} -39.0°$ (c 1.0; 10% CH₃COOH); $R_f = 0.51$ (A, "Eastman"), 0.82 (B, "Eastman"); $E_{His} = 0.34$ (pH=2.4).

Benzyloxycarbonyl-glycyl-N$^\epsilon$-benzyloxycarbonyl-lysyl-prolyl-arginine (5)

(a) 6.33 g (10 mmol) of tert.butyloxycarbonyl-N$^\epsilon$-benzyl-oxycarbonyl-lysyl-prolyl-arginine (3) are treated with 40 ml of a 70% aqueous solution of trifluoroacetic acid for 1.5 hour the reaction progress being controlled by thin-layer chromatography. The solution is evaporated to dryness, the residue is rubbed under ether, filtered-off, dried in vacuum, then dissolved in 200 ml of water and treated with an anionite. The solution is evaporated to dryness. After drying in vacuum there are obtained 5.6 g (quantitatively) of N$^\epsilon$-benzyloxycarbonyl-arginine (4) which has the following properties: R$_f$=0.30 (A, "Eastman"), 0.62 (B, "Eastman"), E$_{His}$=0.76 (pH=2.4).

(b) To a solution of 1.86 g (3.3 mol) of compound (4) in 10 mol of water there is added under stirring a solution of 1.24 g (3.6 mmol) of pentafluorophenyl ester of benzyloxycarbonyl-glycine in 30 ml of dioxane. After 2 hours the solution is evaporated to dryness, the residue is dissolved in 8 ml of dimethylformamide. The reaction mixture is stirred for 72 hours, added with 200 ml of ethyl-acetate and kept for 12 hours in a refrigerator. The resulting precipitate is filtered-off, washed with ethylacetate and ether. The yield of vacuum-dried benzyloxycarbonyl-glycyl-N$^\epsilon$-benzyloxycarbonyl-lysyl-prolyl-arginine (5) is 2.31 g (96%). The compound (5) has the following properties: M.p. 175° C.; [α]$_D^{20}$= −35.1° (c. 1.0; MeOH); R$_f$=0.40 (A, "Merck") 0.74 (B, "Merck"): E$_{His}$=0.36 (pH=2.4).

Glycyl-lysyl-prolyl-arginine (6)

1.0 g (1.39 mmol) of benzyloxycarbonyl-glycyl-N$^\epsilon$-benzyloxycarbonyl-lysyl-prolyl-arginine (5) is hydrogenated under atmospheric pressure in a solution of 20 ml of methanol and 1 ml of acetic acid in the presence of palladium black for 10 hours. The product is purified in a column (2.5×15 cm) with CM-cellulose, eluted with a solution of ammonium acetate with lienarily increasing ionic strength (from 0.01 M, pH 4.5 to 0.1 M, pH 6.7 and then to 0.2 M, pH 6.9).

The elution rate is 60 ml/hr. The volume of fractions is 10 ml. Fractions of 150–220 are collected, evaporated, lyophilized first from ammonium acetate, then from water. The desired product (6) yield is 0.6 g (68%). The product has the following properties: M.p. 110° C. (with decomposition); [α]$_D^{20}$−62.3° (c 0.48; 5% CH$_3$COOH); R$_f$=0.16 (B, "Merck"); E$_{His}$=1.10 (pH=2.4).

What is claimed is:

1. A synthetic analog of tuftisin, viz. glycyl-lysyl-prolyl-arginine of the formula:

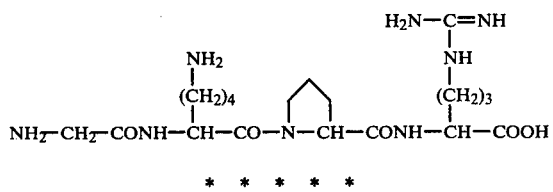

* * * * *